United States Patent [19]
Yoon

[11] Patent Number: 5,810,853
[45] Date of Patent: Sep. 22, 1998

[54] KNOTTING ELEMENT FOR USE IN SUTURING ANATOMICAL TISSUE AND METHODS THEREFOR

[76] Inventor: InBae Yoon, 2101 Highland Ridge Dr., Phoenix, Md. 21131

[21] Appl. No.: 585,875

[22] Filed: Jan. 16, 1996

[51] Int. Cl.⁶ ................................................ A61B 17/08
[52] U.S. Cl. ...................... 606/151; 606/157; 606/158; 606/232
[58] Field of Search ................... 606/158, 157, 606/151, 232; 227/902

[56] References Cited

U.S. PATENT DOCUMENTS

| | | |
|---|---|---|
| 3,091,828 | 6/1963 | Soltis . |
| 3,249,104 | 5/1966 | Hohnstein . |
| 3,446,212 | 5/1969 | Le Roy . |
| 3,541,591 | 11/1970 | Hoegerman . |
| 3,604,425 | 9/1971 | Le Roy . |
| 3,753,438 | 8/1973 | Wood et al. . |
| 3,857,396 | 12/1974 | Hardwick . |
| 3,958,576 | 5/1976 | Komiya . |
| 4,064,881 | 12/1977 | Meredith . |
| 4,169,476 | 10/1979 | Hiltebrandt . |
| 4,217,902 | 8/1980 | March . |
| 4,291,698 | 9/1981 | Fuchs et al. . |
| 4,387,489 | 6/1983 | Dudek . |
| 4,396,139 | 8/1983 | Hall et al. . |
| 4,478,219 | 10/1984 | Rozario et al. . |
| 4,484,581 | 11/1984 | Martin et al. . |
| 4,498,476 | 2/1985 | Cerwin et al. ............ 606/158 |
| 4,548,201 | 10/1985 | Yoon . |
| 4,551,888 | 11/1985 | Beecher ................... 606/151 |
| 4,592,355 | 6/1986 | Antebi . |
| 4,612,932 | 9/1986 | Caspar et al. . |
| 4,637,395 | 1/1987 | Caspar et al. . |
| 4,777,950 | 10/1988 | Kees, Jr. . |
| 4,791,707 | 12/1988 | Tucker . |
| 4,869,268 | 9/1989 | Yoon . |
| 4,961,743 | 10/1990 | Kess, Jr. et al. . |
| 5,026,379 | 6/1991 | Yoon . |
| 5,062,846 | 11/1991 | Oh et al. . |
| 5,078,731 | 1/1992 | Hayhurst . |
| 5,100,418 | 3/1992 | Yoon et al. . |
| 5,160,339 | 11/1992 | Chen et al. . |
| 5,171,250 | 12/1992 | Yoon . |
| 5,171,251 | 12/1992 | Bregen et al. . |
| 5,217,473 | 6/1993 | Yoon . |
| 5,234,449 | 8/1993 | Bruker et al. . |
| 5,236,434 | 8/1993 | Callicrate . |
| 5,282,809 | 2/1994 | Kammerer et al. . |
| 5,282,832 | 2/1994 | Toso et al. . |
| 5,318,578 | 6/1994 | Hasson . |

(List continued on next page.)

OTHER PUBLICATIONS

"Berry & Kohn's Introduction to Operating Room Technique", Lucy Jo Atkinson and Mary Louise Kohn, 1978.

*Primary Examiner*—Michael Powell Buiz
*Assistant Examiner*—Tina T. D. Pham

[57] ABSTRACT

A knotting element for use in surgical procedures to effect a knot in a length of filamentous material includes a body for being attached to a segment of the filamentous material and having opposed legs, an engaging member carried by one of the legs and a recess formed in the other of the legs corresponding to the engaging member. The body is movable from an open position wherein the engaging member is disposed externally of the recess to receive a second segment of the filamentous material to a closed position wherein the engaging member is disposed within the recess to immovably fixate the second segment of filamentous material to the knotting element to effect a knot. A method of effecting a knot in a length of filamentous material includes the steps of providing a knotting element attached to a first segment of a length of filamentous material, placing a second segment of the filamentous material between legs of the knotting element with the knotting element in an open position, positioning the second segment of filamentous material in engagement with an engaging member carried by one of the legs and moving the knotting element to a closed position wherein the engaging member is disposed in the other of the legs to fixedly secure the second segment of the filamentous material to the knotting element to effect a knot.

20 Claims, 3 Drawing Sheets

U.S. PATENT DOCUMENTS

| | | |
|---|---|---|
| 5,330,442 | 7/1994 | Green et al. . |
| 5,330,503 | 7/1994 | Yoon . |
| 5,334,209 | 8/1994 | Yoon . |
| 5,342,373 | 8/1994 | Stefanchik et al. . |
| 5,366,458 | 11/1994 | Korthoff et al. . |
| 5,366,459 | 11/1994 | Yoon . |
| 5,376,101 | 12/1994 | Green et al. . |
| 5,383,905 | 1/1995 | Golds et al. . |
| 5,391,174 | 2/1995 | Weston . |
| 5,409,499 | 4/1995 | Yi . |
| 5,464,416 | 11/1995 | Steckel . |

FIG.12

KNOTTING ELEMENT FOR USE IN SUTURING ANATOMICAL TISSUE AND METHODS THEREFOR

BACKGROUND OF THE INVENTION

1. Field of the Invention

The present invention pertains to suturing of bodily tissue and, more particularly, to methods and apparatus for suturing tissue during endoscopic and open surgical procedures.

2. Discussion of the Prior Art

Suturing of bodily tissue is a time consuming part of most surgical procedures including both open surgery and endoscopic or minimally invasive surgery. By open surgery is meant surgery wherein the surgeon gains access to the surgical site via a relatively large incision, and by endoscopic surgery is meant surgery wherein the surgeon gains access to the surgical site via one or more portals through which endoscopes are introduced to view the surgical site and through which various instruments are introduced to the surgical site. There are many common endoscopic surgical procedures, including arthroscopy, laparoscopy (pelviscopy), gastroentroscopy and laryngobronchoscopy, for example. In the past, suturing has been accomplished with the use of a sharp metal suture needle attached to the end of a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed; however, knotting of the suture material is time consuming and tedious work, particularly in microsurgery and endoscopic surgery. In microsurgery, suturing is necessarily time consuming due to the limited space at the suture site, the small size of the suture needle and the suture material and the concomitant difficult manipulation required to pass the suture needle through the tissue and to tie a knot in the suture material. With respect to endoscopic surgery, suturing and tying knots represents an even more time consuming procedure due to the difficult maneuvers required. Accordingly, while endoscopic surgery would be preferred for most procedures, the advantages can be outweighed by the disadvantages caused by the length of time required to complete the endoscopic surgical procedure, which time is greatly extended due to the time required for suturing. It is extremely important for knotting or tying of sutures to be consistently performed to provide a stitch with controlled, non-slipping tension; and, to this end, it is common for surgeons to tie double knots, that is, a first knot to control tension and a second knot to secure the first knot. Accordingly, it will be appreciated that there is a great need for improving the tying procedure involved in suturing to permit expedited knotting while also providing consistent, secure knots.

There have been many attempts to provide devices to take the place of conventional suturing with a suture needle and a length of suture material; however, such devices have essentially been staples, clips or clamps not facilitating adjustment of tension by the surgeon. French Patent No. 2,651,113 to Alain and U.S. Pat. No. 3,123,077 to Alcamo, No. 3,570,497 to Lemole, No. 4,548,202 to Duncan, No. 4,592,355 to Antebi, No. 4,730,615 to Sutherland et al, No. 4,935,028 to Drews, No. 4,950,285 to Wilk, No. 4,955,913 to Robinson and No. 5,123,913 to Wilk are representative of devices for use during open surgery to adjustably hold tissue together similar to suturing and tying but fail to provide the same feel and tension control as tying or knotting a length of suture material. U.S. Pat. No. 3,910,281 to Kletschka et al is representative of suture anchors for facilitating tying. U.S. Pat. No. 2,075,508 to Davidson, No. 2,199,025 to Conn and No. 3,664,345 to Dabbs et al are illustrative of suture buttons for retaining sutures. U.S. Pat. No. 3,976,079 to Samuels et al and 4,291,698 to Fuchs, deceased, et al, are representative of suture buttons having structure for clamping suture material. U.S. Pat. No. 4,750,492 to Jacobs discloses apparatus and method for suturing utilizing both an anchor and a clenching device.

Endoscopic surgery is preferred over open surgery due to the greatly reduced trauma and wound healing time for the patient and due to concomitant cost savings associated with shorter hospital stays and performing surgery in non-hospital or out-patient surgery sites. Accordingly, there has been much effort spent to develop techniques for facilitating the suturing normally performed by use of a suture needle and a length of suture material. Alternative techniques proposed have included electrical coagulation, mechanical devices such as clips, clamps and staples, and lasers; however, no alternative technique has yet been well accepted by surgeons to produce the results obtained by suturing and tying. Thus, there is a great need for suturing techniques useful in endoscopic surgery to permit surgeons to suture with controlled tension and approximation of tissue similar to that obtained by conventional knot tying.

U.S. Pat. No. 3,541,591 to Hoegerman, No. 3,753,438 to Wood et al, and No. 3,775,825 to Wood et al disclose apparatus and methods for suturing wherein clips are secured on the free ends of a suture filament. U.S. Pat. No. 5,078,731 to Hayhurst, No. 5,160,339 to Chen et al, No. 5,171,251 to Bregen et al, No. 5,234,449 to Bruker et al, No. 5,282,832 to Toso et al and No. 5,330,442 to Green et al are representative of clips for clamping suture material to eliminate knotting during endoscopic procedures. European Patent Publication No. 0 477 020A to Chen et al and U.S. Pat. No. 5,015,250 to Foster, No. 5,037,433 to Wilk et al, No. 5,059,201 to Asnis, No. 5,084,058 to Li, No. 5,087,263 to Li, No. 5,100,415 to Hayhurst, No. 5,100,421 to Christoudias, No. 5,144,961 to Chen, No. 5,147,373 to Ferzli, No. 5,152,769 to Baber and No. 5,163,946 to Li are representative of needle holders and apparatus for suturing, knotting or ligating during endoscopic procedures. The above techniques and instruments have the disadvantages of requiring complex instruments, of requiring special suture devices, of being difficult to manipulate and/or of not sufficiently reducing the time required for suturing and tying or knotting.

U.S. Pat. No. 4,932,962, No. 4,981,149, No. 5,074,874 and No. 5,100,418 to Yoon et al and U.S. Pat. No. 4,935,027, No. 5,053,047, No. 5,222,976, No. 5,330,503 and No. 5,366,459 to Yoon disclose methods and apparatus particularly useful for suturing during endoscopic procedures to permit tissue approximation with controlled tension.

SUMMARY OF THE INVENTION

Accordingly, it is a primary object of the present invention to overcome the aforementioned disadvantages of the prior art.

Another object of the present invention is to provide a knotting element attached to a length of filamentous material and having opposed legs and an engaging member on one of the legs for engaging a segment of the filamentous material when the legs are in an open position and for being disposed within the other of the legs when the legs are in a closed position to immovably fixate the segment of filamentous material.

A further object of the present invention is to engage the segment of filamentous material with the engaging member while permitting adjustment of the knotting element relative to the filamentous material when the legs are in the open position.

The present invention has as another object to provide a space between the engaging member and the one leg for positioning the segment of filamentous material between the engaging member and the one leg, with the space being disposed within the other leg when the legs are in the closed position to prevent disengagement of the segment of filamentous material from the engaging member.

A still further object of the present invention is to provide a knotting element attached to a first segment of a length of filamentous material, to engage a second segment of the length of filamentous material with an engaging member of the knotting element when the knotting element is in an open position and to move the knotting element to a closed position wherein the engaging member is disposed within the knotting element to fixedly secure the second segment of filamentous material.

An additional object of the present invention is to plastically deform the knotting element to cause the engaging member to enter the other leg.

Some of the advantages of the present invention are that the knotting element can be utilized in many various procedures including suturing and ligation, one or more engaging members can be oriented in many various ways for optimal positioning in accordance with procedural use, the engaging members can be attached to one or more segments of the filamentous material either movably or fixedly when the knotting element is in the open position, the knotting elements take the place of conventional knot-tying and provide redundant protection similar to that obtained with the tying of multiple knots, the knotting elements can be locked in the closed position and/or movable to a further closed position, and the knotting elements do not present any exposed sharp edges.

These and other objects, advantages and benefits are realized with the present invention as characterized in a knotting element attached to a first segment of a length of filamentous material and having a body defining opposed legs with inner surfaces. An engaging member protrudes from the inner surface of one of the legs, and a recess is formed in the other of the legs along the inner surface thereof for receiving the engaging member. The knotting element is movable from an open position wherein the inner surfaces are spaced from one another such that the engaging member is disposed externally of the recess to a closed position wherein the engaging member is disposed within the recess. A passage is defined between the engaging member and the associated inner surface for receiving a second segment of the length of filamentous material when the knotting element is in the open position, thereby attaching the second segment of filamentous material to the knotting element. When the knotting element is moved from the open position to the closed position, the engaging member enters the recess to immovably fixate the second segment of the length of filamentous material to the knotting element to effect a knot. A method of effecting a knot during surgical procedures according to the present invention includes the steps of providing a knotting element attached to a first segment of a length of filamentous material, placing a second segment of the length of filamentous material between legs of the knotting element with the knotting element in an open position, placing a second segment of the length of filamentous material in engagement with an engaging member disposed between the legs and moving the knotting element to a closed position wherein the engaging member enters a recess in the knotting element to fixedly secure the second segment of the filamentous material to the knotting element to effect a knot.

Inasmuch as the present invention is subject to many variations, modifications and changes in detail, it is intended that all subject matter discussed above or shown in the accompanying drawings be interpreted as illustrative only and not be taken in a limiting sense.

DESCRIPTION OF THE PREFERRED EMBODIMENTS

Figures 1, 2, 3, 8, 9:
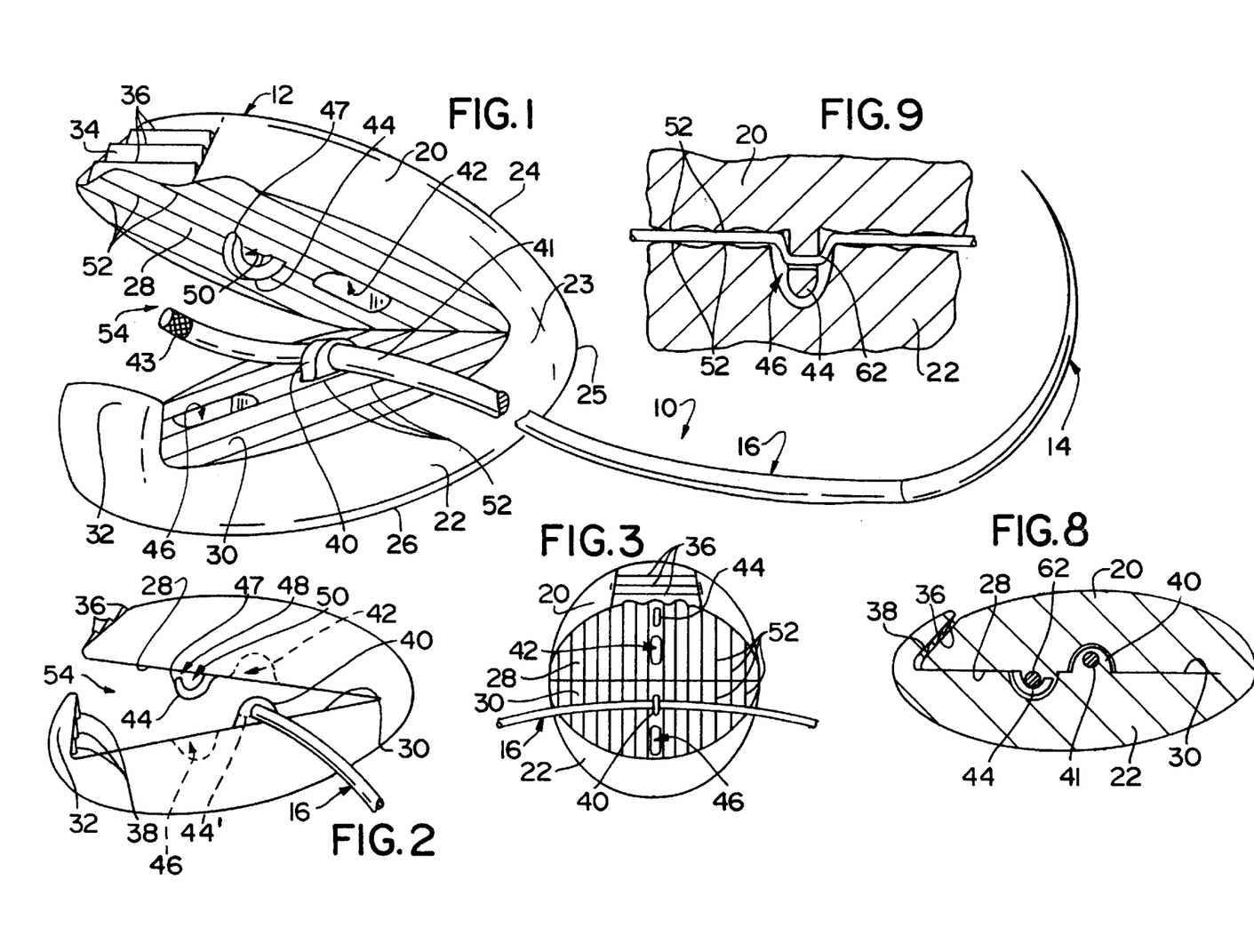
FIG. 1 is a broken perspective view of a knotting element according to the present invention incorporated in a suture apparatus.
FIG. 2 is a broken side view of the suture apparatus showing the knotting element in the open position.
FIG. 3 is a broken front view of the suture apparatus showing the knotting element in the open position.
FIG. 8 is a side sectional view of the knotting element in the closed position.
FIG. 9 is a broken sectional view of the knotting element in the closed position.

FIG. 1 illustrates a knotting element 12 according to the present invention for use in the various apparatus and methods for suturing and ligating tissue disclosed in applicant's co-pending prior U.S. applications Ser. No. 08/366,285 filed Dec. 29, 1994, Ser. No. 08/377,723 filed Jan. 25, 1995, Ser. No. 08/401,002 filed Mar. 9, 1995 and Ser. No. 08/531,153 filed Sep. 15, 1995 incorporated herein by reference. Knotting element 12 is illustrated in FIG. 1 in a suture apparatus 10 comprising a suture supply and a needle 14 coupled with the suture supply. The suture supply includes one or more knotting elements 12 and a length of filamentous suture material 16 carrying knotting elements 12, the suture supply for suture apparatus 10 including a single knotting element 12. The suture material 16, which is coupled to needle 14, can be of any conventional filamentous construction, such as a monofilament or multifilament strand or thread. The suture material can have a length dependent upon the type of stitch to be performed when a single knotting element is carried by the suture material; and, when a plurality of knotting elements are carried by the suture material, the length of the suture material can correspond to the number of stitches expected to be made or can be essentially indefinite by utilizing a package, such as a spool having the suture material wound therearound. The suture material can be solid or hollow; and, when the suture material is hollow, small holes can be formed in the wall of the suture material to communicate with the hollow interior thereof. Various substances, such as medicaments, can be supplied within the hollow interior of the suture material to leach out through the holes and enter tissue in which the suture material is placed. The suture material can be made of non-stretchable or stretchable, bioabsorbable or non-bioabsorbable materials, and the suture material can have various outer diameter or cross-sectional sizes in accordance with procedural use including sizes suitable for use in microsurgical procedures.

The knotting element 12 includes a body formed of a medical grade, bioabsorbable or non-bioabsorbable, plastically deformable or malleable material. The body has a configuration defining angularly oriented, opposed legs or jaws 20 and 22 connected to one another by a curved base 23. Legs 20 and 22 each have a partial oval contour or configuration with curved or rounded outer surfaces 24 and 26, respectively, merging with a curved or rounded outer surface 25 of base 23 and with opposed, inner surfaces 28 and 30, respectively, converging at base 23. A locking protrusion 32 at a distal end of one of the legs, i.e. leg 22 in FIG. 1, extends inwardly toward the other leg and is angled slightly proximally toward base 23. The other or opposite leg, i.e. leg 20 in FIG. 1, terminates distally at an outer angled end surface 34. A plurality of locking members 36, formed as teeth or protrusions, are formed on end surface 34, and a plurality of locking members 38, formed as corresponding teeth or protrusions, are formed on an inner surface of protrusion 32 for locking engagement with teeth 36 when the knotting element 12 is moved from an open position to a closed position as explained further below. Protrusion 32 has a curved or rounded outer surface such that the knotting element 12 forms a smooth profile in the closed position to avoid damage to surrounding anatomical tissue.

A lug 40 protrudes from inner surface 30, and a recess 42 is formed in leg 20 along inner surface 28 opposite lug 40. Lug 40 has a passage therein receiving a first segment 41 of the length of suture material 16 such that the suture material extends from lug 40 in a direction transverse to a longitudinal axis of knotting element 12. Accordingly, lug 40 defines an attachment site at which the knotting element 12 is carried by or attached to a first segment of the suture material either by immovable fixation or by a movable fixation or sliding engagement; and, in the case of suture apparatus 10, the knotting element 12 is immovably attached to the first segment of the length of suture material 16 at lug 40. The first segment of suture material can extend entirely through lug 40, partly through lug 40 or can terminate at lug 40. In the case of knotting element 12, the suture material extends entirely through lug 40 to pass entirely through the knotting element in the transverse direction and terminates proximally at a rigid tail 43.

A hook, retaining or engaging member 44 protrudes from inner surface 28, and a corresponding recess 46 is formed in leg 22 along inner surface 30 opposite hook member 44. Hook member 44 defines a curved hook, finger or catch curving inwardly and distally from inner surface 28 in a concave manner. The hook includes a first end attached to inner surface 28, a second or distal end 47 spaced from inner surface 28 to define a space or opening 48 between the end 47 and the inner surface 28 and a curved segment between the first and second ends defining an innermost end. Opening 48, which faces distally in knotting element 12, communicates with a passage 50 defined between surface 28 and an inner surface of the curved segment of hook member 44. Passage 50 is of a size to receive or accommodate the cross-sectional size of the filamentous material, and passage 50 can be of a size to frictionally or closely or snugly receive the filamentous material. Opening 48 is of a size just large enough to permit a second segment of the length of suture material 16 to be positioned in passage 50, in which case the suture material extends from hook member 44 in a direction transverse to the longitudinal axis of the knotting element 12 while being captured, held or retained in passage 50 by hook member 44. Opening 48 is smaller in cross-sectional size than passage 50, and opening 48 can be of a size to prevent withdrawal of the filamentous material from passage 50 in the absence of a manual withdrawal force applied thereto. Inner surfaces 28 and 30 are configured or provided with gripping ridges 52 extending in a direction transverse to the direction in which the suture material extends, i.e. in the direction of the knotting element longitudinal axis in the case of knotting element 12. It should be appreciated that no lugs and only hook members can be provided in knotting element 12 as shown in dotted lines in FIG. 2 wherein lug 40 is replaced with hook member 44'.

The lug 40, hook member 44 and recesses 42 and 46 are arranged such that each inner surface has a lug or a hook member and a recess longitudinally aligned with the lug or the hook member and with the lug or hook member of each inner surface positioned to be received in the recess of the opposite inner surface when the knotting element is moved from the open position to the closed position as explained further below. As shown in FIGS. 1, 2 and 3, knotting element 12 is normally disposed in an open position with inner surfaces 28 and 30 spaced from one another to define a mouth 54 therebetween and with lug 40 and hook member 44 not received in recesses 42 and 46, respectively. Accordingly, lug 40 and hook member 44 are disposed in mouth 54 between inner surfaces 28 and 30 with opening 48 and passage 50 disposed externally of recess 46. Recesses 42 and 46 have configurations corresponding to the external configurations of lug 40 and hook member 44, respectively, to closely or snugly receive lug 40 and hook member 44, respectively, in the manner of a friction, press or snap fit. The knotting element 12 can be formed of any suitable medical grade materials including metals, plastics and rubbers as well as bioabsorbable and non-bioabsorbable materials.

Needle 14, which can be curved as shown in FIG. 1, is coupled with the length of suture material 16 and has a distal end 56 for penetrating anatomical tissue. In the case of suture apparatus 10, a distal end of the suture material 16 is coupled with a proximal end of needle 14; however, the attachment position at which the suture material is coupled to the needle can be anywhere along the body of the needle. The needle can have various configurations including curved, circular, arcuate, decreasing and increasing spiral, straight and bent configurations. When the needle is to be used with a suture supply having a length of suture material carrying a plurality of knotting elements, the needle is preferably hollow to have a lumen through which the suture material passes. Where the knotting elements have a size larger than the lumen of the needle and are not compressible, a longitudinal slot is provided in communication with the lumen of the needle to allow the knotting elements to pass externally along the needle while the suture material passes internally through the needle lumen as disclosed in the prior applications. Where the knotting elements are compressible, the knotting elements can pass through the needle lumen along with the suture material without the need for a slot in the needle; and, similarly, no slot is required where the knotting elements have a size to pass through the lumen as also disclosed in the prior applications.

Figure 4:
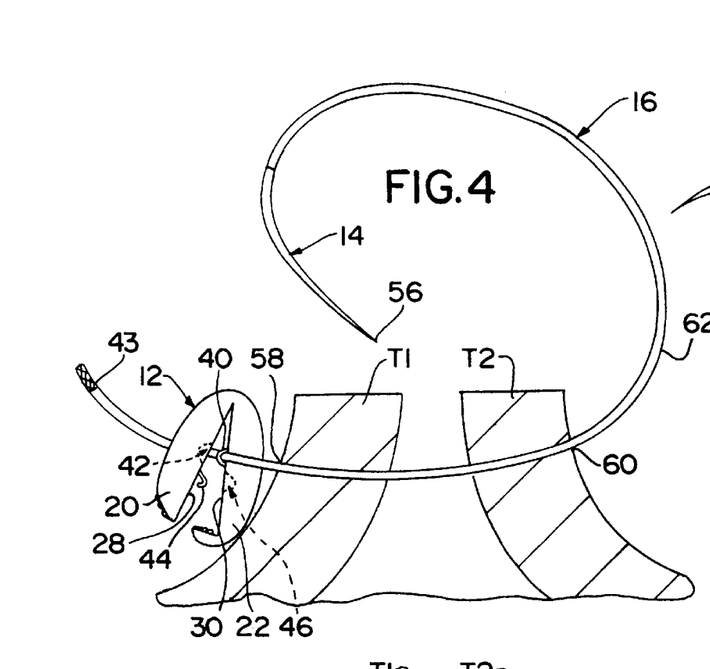
FIG. 4 is a broken side view, partly in section, illustrating a first step in a method of suturing utilizing the suture apparatus.
Figure 5:
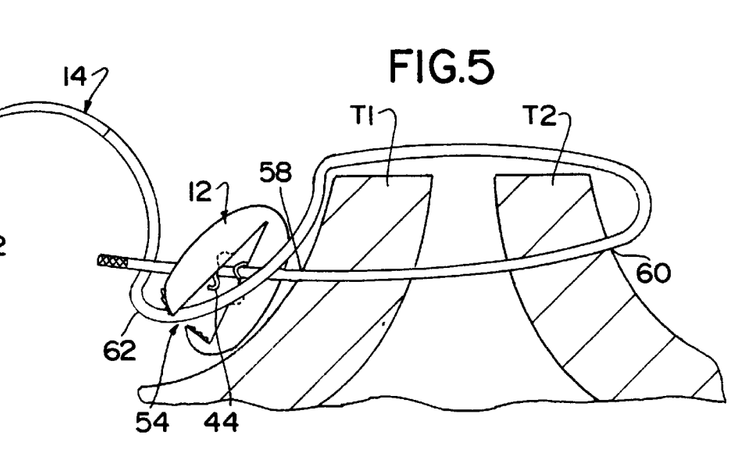
FIG. 5 is a broken side view, partly in section, illustrating a second step in a method of suturing utilizing the suture apparatus.
Figure 6:
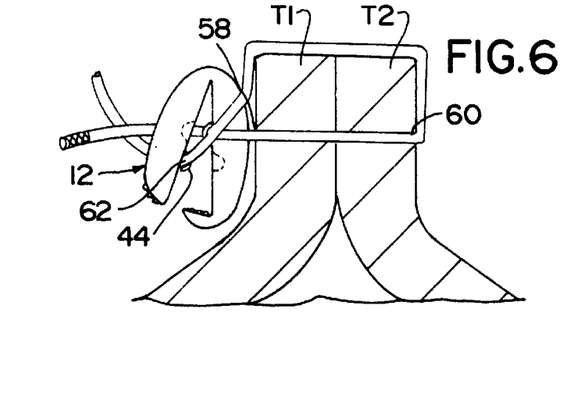
FIG. 6 is a broken side view, partly in section, illustrating a third step in a method of suturing utilizing the suture apparatus.
Figure 7:
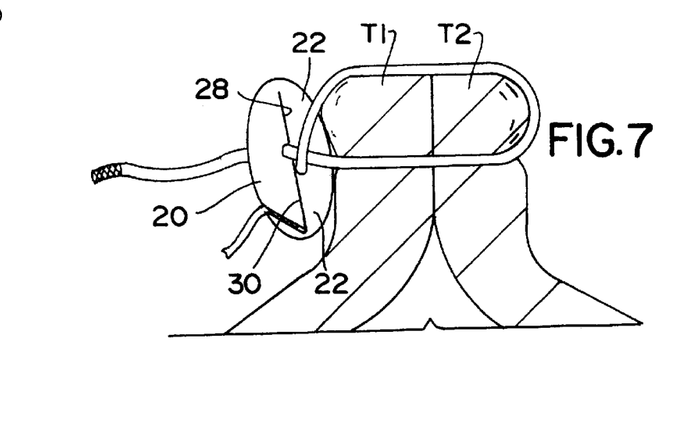
FIG. 7 is a broken side view, partly in section, illustrating a fourth step in a method of suturing utilizing the suture apparatus.
Figures 10, 11, 12:
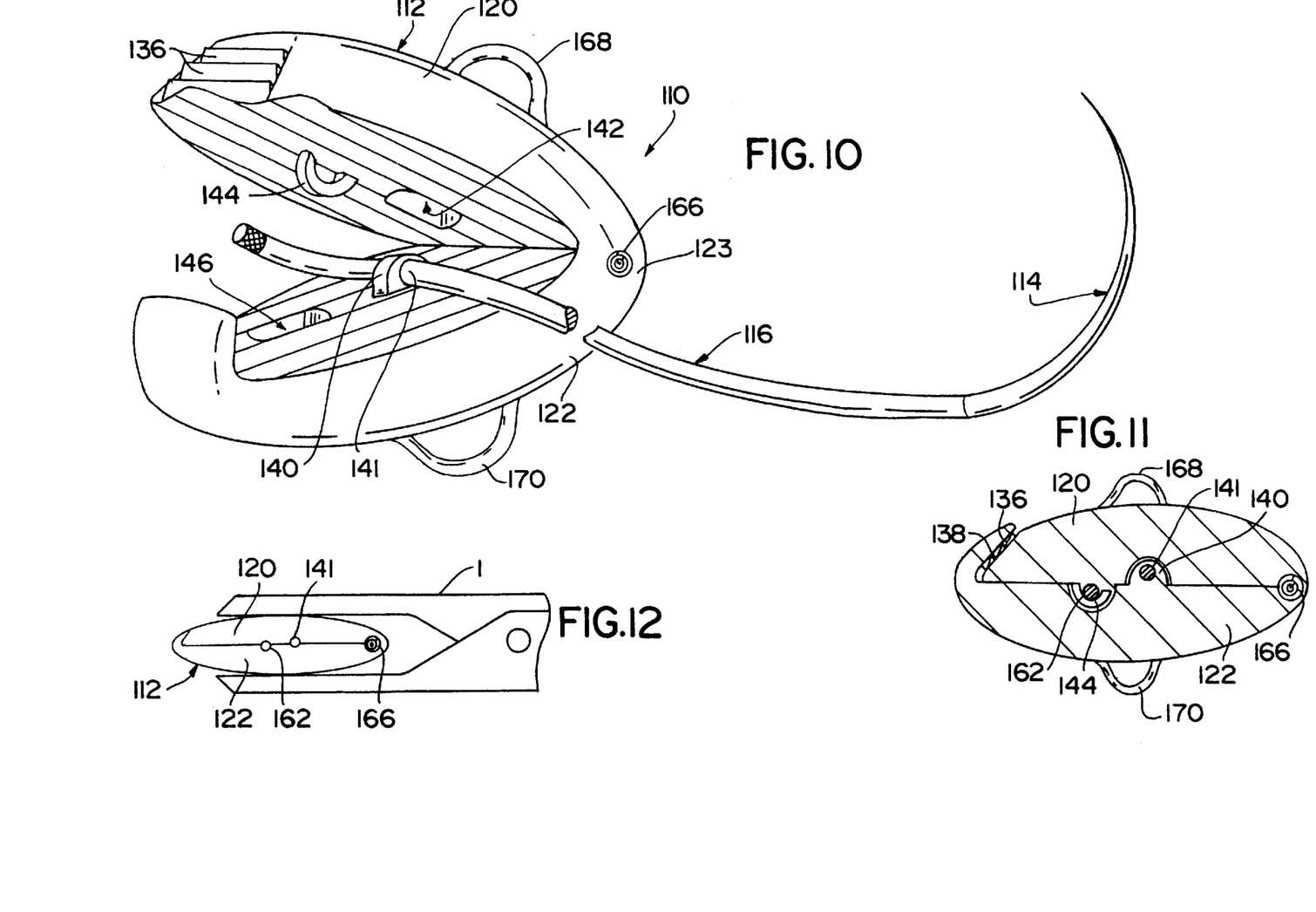
FIG. 10 is a broken perspective view of an alternative embodiment of a knotting element according to the present invention incorporated in a suture apparatus.
FIG. 11 is a side sectional view showing the knotting element of FIG. 10 in the closed position.
FIG. 12 is a broken side view showing the knotting element of FIG. 11 in a further closed position.

FIGS. 4–7 illustrate one method of use of the suture apparatus 10 during which the needle 14 can be manipulated with a needle holder (not shown) or another instrument as described in prior application Ser. No. 08/366,285 incorporated herein by reference. To suture tissue portions T1 and T2, the needle tip 56 is driven distally or forwardly through an entry point 58 in tissue portion T1 and then through tissue portion T2 and out of tissue portion T2 at an exit point 60 carrying the suture material 16 through the tissue portions as shown in FIG. 4. Once needle 14 has passed through tissue portion T2, the segment 62 of suture material extending from exit point 60 is pulled until the knotting element 12 contacts or is adjacent tissue portion T1 at the entry point 58. Segment 62 is drawn back over tissue portions T1 and T2 to the entry point 58. The segment 62 is positioned in mouth 54 as shown in FIG. 5 and then in passage 50 defined by hook member 44, the segment 62 being placed in the passage 50 via opening 48 as shown in FIG. 6. Accordingly, the segment 62 of suture material will be movably captured, retained or held by hook member 44 such that an adjustable stitch is formed extending from the knotting element 12 through the tissue portions T1 and T2 and back to the knotting element 12 with the knotting element effecting or serving as a knot for the suture stitch. Tension is applied to the suture material to tighten the suture stitch to adjustably approximate tissue portions T1 and T2 as shown in FIG. 7. Knotting element 12 is plastically deformed, "crunched" or "crushed" with a grasping instrument for movement from the open position to the closed position as disclosed in prior application Ser. No. 08/366,285 and as illustrated in FIG. 12 for movement of knotting element 112 to a further closed position. Movement of knotting element 12 to the closed position causes legs 20 and 22 to be moved toward one another such that lug 40 and hook member 44 enter the corresponding recesses 42 and 46, respectively, as shown in FIGS. 7 and 8. In the closed position, the inner surfaces 28 and 30 of the legs are disposed adjacent one another with locking teeth 36 engaged with locking teeth 38 to lock the knotting element in the closed position. The first segment of suture material extending through lug 40 will be fixedly secured to knotting element 12 at the attachment site, and the second segment 62 will be fixedly secured to the knotting element 12 at a grasping site defined by hook member 44 received in recess 46. As shown in FIG. 9 for second segment 62, the first and second segments of suture material extending through lug 40 and hook member 44, respectively, are held by ridges 52 and are bent since the passages of the lug and hook member are disposed within the associated or corresponding recess such that the segments of suture material extend into and out of the associated recesses for secure fixation and redundant protection. In addition, the opening 48 is disposed within the recess 46 to prevent disengagement of the suture material from the hook member 44 and the innermost end of the hook member 44 is entirely, internally disposed within the leg 22.

The locking protrusion 32 overlaps or extends over the angled end surface 34, and the knotting elements have a substantially oval profile or contour with no sharp edges. The tail 43 and any excess suture material can be severed from the knotting element subsequent to formation of the stitch.

An alternative embodiment of a knotting element according to the present invention is illustrated at 112 in FIG. 10 incorporated in a suture apparatus 110. Suture apparatus 110 is similar to suture apparatus 10 and includes a suture supply comprising knotting element 112 and a length of filamentous material 116 carrying knotting element 112 and a needle 114 coupled with the suture supply. Knotting element 112 is substantially the same as knotting element 12 except that knotting element 112 is spring-biased or spring-loaded to be normally disposed in the closed position illustrated in FIG. 11 and except that knotting element 112 is movably attached to the first segment of filamentous material to be slidable when the knotting element is in the open position shown in FIG. 10. Accordingly, knotting element 112 includes lug 140 slidably receiving a first segment 141 of the filamentous material in the passage of lug 140 to movably attach the first segment of filamentous material to the knotting element 112 at an attachment site defined by lug 140. Knotting element 112 has a spring 166, such as a coil or torsion spring, disposed at base 123 and connected between legs 120 and 122 to bias the knotting element 112 to the closed position. Various types of springs can be utilized to bias the knotting element 112 to be normally disposed in the closed position, and the springs can be disposed externally of or within the body of the knotting element. In addition to the use of separate or distinct springs, it should be appreciated that the knotting element itself can be made of spring materials or with a shape memory biasing the knotting element to the closed position. Engaging members 168 and 170 in the form of protruding ears or handles are disposed along the outer surfaces of legs 120 and 122, respectively, for being grasped to move the knotting element from the closed position to the open position shown in FIG. 10 and as described in the aforementioned prior applications incorporated herein by reference. Knotting element 112 is illustrated as having locking teeth 136 and 138 for redundant fixation with the spring closure force; however, it should be appreciated that the locking teeth 136 and 138 need not be provided. Knotting element 112 is made of plastically deformable or malleable material to be compressed, "crushed" or "crunched" for movement to a further closed position shown in FIG. 12 and as explained further below and in the prior applications.

During one manner of use of suture apparatus 110, the first segment 141 of filamentous material 116 attached to knotting element 112 at lug 140 will be immovably fixed to the knotting element when the knotting element is in the normally closed position. The knotting element 112 is moved from the normally closed position to the open position by application of an opening force, via engaging members 168 and 170, sufficient to overcome the closing force of spring 166 as well as the locking force of teeth 136 and 138 where the locking teeth are provided. With the knotting element 112 moved to the open position shown in FIG. 10, the lug 140 and the hook member 144 will be moved out of recesses 142 and 146, respectively. Accordingly, the knotting element 112 can be selectively moved along the length of filamentous material 116 in accordance with the procedure to be performed. With the knotting element 112 held in the open position, another segment 162 of the length of filamentous material is positioned in the passage of hook member 144 to be movably held thereby. When it is desired to immovably fixate both segments 141 and 162 of filamentous material to the knotting element, the opening force on the knotting element is removed or released, such as by releasing the engaging members 168 and 170, causing the knotting element to return automatically to the closed position. Once the segments 141 and 162 of the filamentous material have been immovably secured to the knotting element 112, the knotting element 112 can be plastically deformed, compressed, "crushed" or "crunched" with instrument I for movement to a further closed position as shown in FIG. 12 for additional securement and protection. Various types of instruments can be utilized to engage the engaging members when opening the knotting element 112 as described in the aforementioned prior applications as well as in prior application Ser. No. 08/401,002 filed Mar. 9, 1995 and incorporated herein by reference.

In addition to the procedures described above, the knotting elements according to the present invention can be used in the various other procedures such as the various procedures described in the prior applications incorporated herein by reference. For example, the suture apparatus can be used to form a loop segment of the suture material extending from tissue portion T2. The loop segment, as well as the segment of suture material extending from tissue portion T1, can be placed within the hook member of the knotting element. An alternative procedure involves placing the loop segment behind or around the knotting element and positioning only the segment extending from tissue portion T1 in the hook member of the knotting element. As a further alternative, the loop segment can be placed within the hook member of the knotting element, and the segment of suture material extending from tissue portion T1 is passed through the loop segment. Where the suture supply includes a plurality of knotting elements carried by the length of suture material, the suture supply can be coupled with a hollow needle which is driven through tissue portions T1 and T2 to exit tissue portion T2. The needle is backed out through tissue portions T1 and T2 to exit the tissue portions at the entry point and is moved proximally until the distal end of the needle is positioned just proximally of the distalmost knotting element. The suture material is pulled through the tissue until the distalmost knotting element is adjacent or in contact with tissue portion T1, and the segment of suture material extending from the exit point is positioned in the hook member of the knotting element. One or more knotting elements can be carried by first and second length portions of filamentous suture material such that two length portions of suture material extend between a knotting element and the needle and/or between adjacent knotting elements to define one or more contractible loops. Accordingly, the needle is driven distally through tissue portions T1 and T2 and is passed through the contractible loop defined by the first and second length portions. The length portions are pulled to contract, tighten or close the loop, and the segments of the suture material length portions passing through the loop are positioned within the hook of the knotting element.

The knotting elements according to the present invention can also be utilized without a needle in various ligating procedures as disclosed in the prior applications incorporated herein by reference. For example, the knotting elements of the present invention can be utilized with one or more lengths of filamentous material to define one or more contractible loops. The knotting element can be movably attached to the filamentous material to allow the contractible loops to be reduced in size, contracted or tightened around anatomical tissue to form ligatures when the knotting elements are in the open position. Once the ligatures are formed with a desired tension, the knotting elements are moved to the closed position and plastically deformed to secure the thusly formed ligatures.

It should be appreciated that the knotting elements according to the present invention can be attached to the filamentous material in many various ways and that the length of filamentous material can terminate at the knotting elements or pass entirely or partly through the knotting elements. The filamentous material can be attached to or terminate at the knotting elements at various locations thereon, and the mouths of the knotting elements can be positioned or oriented to optimally position the knotting elements in accordance with procedural use. Although the knotting elements have been illustrated herein with a lug, it should be appreciated that no lugs need be provided in the knotting elements in that the hook members can be provided in place of the lugs. The knotting elements can be provided with any number of lugs and/or hook members, and the lugs and/or hook members can be provided anywhere along one or both of the inner surfaces of the knotting elements. Where no lugs and only hook members are provided in the knotting elements, the knotting elements can be moved along the filamentous material prior to being moved to the closed position. Accordingly, the filamentous material remains held by the knotting elements during the procedure being performed and thusly facilitates the performance of various endoscopic and open suturing and ligating procedures. The spaces or openings at the free or unattached ends of the hook members can face in any direction to optimally position the hook members to receive the filamentous material in accordance with procedural use, and the hook members can face in opposite directions.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A knotting element for use in surgical procedures to effect a knot in a length of filamentous material comprising a body for being attached to a segment of the length of filamentous material and defining a pair of opposed legs having opposed inner surfaces, at least one hook member extending inwardly from one of said inner surfaces and having an innermost end and at least one recess along the other of said inner surfaces corresponding to said hook member, said body being movable from an open position wherein said inner surfaces are spaced from one another with said hook member disposed externally of said recess to a closed position wherein said inner surfaces are adjacent one another with said hook member disposed within said recess, said innermost and of said hook member being entirely, internally disposed within said leg having said recess when said body is in said closed position, said hook member holding another segment of the length of filamentous material between said hook member and said one of said inner surfaces when said body is in said open position whereby, when said body is moved to said closed position, the another segment of the length of filamentous material is immovably held within said recess.

2. A knotting element as recited in claim 1 wherein said hook member has a curved configuration.

3. A knotting element as recited in claim 2 wherein said recess has a configuration corresponding to said configuration of said hook member.

4. A knotting element as recited in claim 3 wherein said legs have curved outer surfaces and said body includes a base connecting said legs to one another and having a curved outer surface merging with said outer surfaces of said legs.

5. A knotting element as recited in claim 4 wherein said inner surfaces converge at said base.

6. A knotting element as recited in claim 5 wherein said body has an oval external configuration in said closed position.

7. A knotting element as recited in claim 6 and further including locking structure on said legs for locking said body in said closed position.

8. A knotting element as recited in claim 6 wherein said body is normally disposed in said open position and is plastically deformable for movement to said closed position.

9. A knotting element for use in surgical procedures to effect a knot in a length of filamentous material comprising a body for being attached to a segment of the length of filamentous material and defining a base, a pair of opposed legs connected to one another at said base and having opposed inner surfaces converging at said base, at least one hook member extending inwardly from one of said inner surfaces and having an innermost end and at least one recess along the other of said inner surfaces corresponding to said hook member, said legs having curved outer surfaces, said base having a curved outer surface merging with said outer surfaces of said legs, said body being movable from an open position wherein said inner surfaces are spaced from one another with said hook member disposed externally of said recess to a closed position wherein said inner surfaces are adjacent one another with said hook member disposed within said recess, said innermost end of said hook member being entirely, internally disposed within said leg having said recess when said body is in said closed position, said body having an oval external configuration in said closed position, said hook member having a curved configuration extending from said one of said inner surfaces to hold another segment of the length of filamentous material between said hook member and said one of said inner surfaces when said body is in said open position, said recess having a configuration corresponding to said configuration of said hook member whereby, when said body is moved to said closed position, the another segment of the length of filamentous material is immovably held within said recess, said body being normally disposed in said closed position and being movable to said open position with an opening force applied to said body, said body returning to said closed position upon release of said opening force.

10. A knotting element as recited in claim 9 wherein said body is plastically deformable for movement to a further closed position.

11. A knotting element for use in surgical procedures to effect a knot in a length of filamentous material comprising a body for being attached to a first segment of the length of filamentous material and defining a pair of opposed legs having opposed inner surfaces, an engaging member protruding inwardly from one of said inner surfaces and having an innermost end and a recess along the other of said inner surfaces for receiving said engaging member, said engaging member curving inwardly from said one inner surface to define a passage between said engaging member and said one inner surface for receiving a second segment of the length of filamentous material, said body being movable from an open position wherein said passage is disposed between said inner surfaces to allow the second segment of the length of filamentous material to be positioned in said passage to a closed position wherein said passage and the second segment of the length of filamentous material are disposed within said recess and said innermost end of said engaging member is entirely, internally disposed within said leg having said recess whereby the length of filamentous material is bent by said engaging member into said recess to immovably fix said body to the length of filamentous material.

12. A knotting element as recited in claim 11 wherein said body defines a mouth between said inner surfaces in said open position and said passage is disposed within said mouth when said body is in said open position.

13. A knotting element as recited in claim 12 wherein said body includes a longitudinal axis and said passage is oriented to receive the length of filamentous material with the length of filamentous material extending in a direction transverse to said longitudinal axis.

14. A knotting element as recited in claim 13 and further including longitudinally extending ridges on said inner surfaces.

15. A knotting element as recited in claim 11 wherein said passage slidably receives the second segment of the length of filamentous material when said body is in said open position.

16. A knotting element as recited in claim 15 wherein said legs each include a distal end and further including locking teeth on said distal ends for locking engagement when said body is in said closed position.

17. A knotting element as recited in claim 15 and further including a lug protruding from one of said inner surfaces and having a passage therethrough for receiving the first segment of the length of filamentous material and a recess along the other of said inner surfaces for receiving said lug when said body is in said closed position.

18. A method of effecting a knot in a length of filamentous material during surgical procedures comprising the steps of
providing a knotting element attached to a first segment of a length of filamentous material and having opposed legs with opposed inner surfaces, respectively, an engaging member extending inwardly from one of the inner surfaces and having an innermost end and a recess formed in the other of the inner surfaces for receiving the engaging member, the knotting element having an open position wherein the legs are spaced from one another and the engaging member is disposed between the legs externally of the recess, the engaging member defining a passage between the engaging member and the one inner surface;

placing a second segment of the length of filamentous material between the legs of the knotting element with the knotting element in the open position;

positioning the second segment of the length of filamentous material in the passage to be held between the engaging member and the one inner surface; and moving the knotting element from the open position to a closed position wherein the legs are adjacent one another and the engaging member and the second segment of the length of filamentous material are disposed in the recess with the innermost end of the engaging member entirely internally, disposed within the leg having the recess to fixedly secure the second segment of the length of filamentous material to the knotting element to effect a knot in the filamentous material.

19. A method of effecting a knot as recited in claim 18 wherein said step of moving includes plastically deforming the knotting element.

20. A method of effecting a knot in a length of filamentous material during surgical procedures comprising the steps of providing a knotting element attached to a first segment of a length of filamentous material and having opposed legs, an engaging member carried by one of the legs and a recess formed in the other of the legs for receiving the engaging member, the knotting element being disposed in a closed position wherein the legs are adjacent one another and the engaging member is disposed in the recess to be entirely, internally disposed within the leg having the recess, the knotting element being movable from the closed position to an open position wherein the legs are spaced from one another and the engaging member is disposed externally of the recess;

moving the knotting element from the closed position to the open position;

placing a second segment of the length of filamentous material between the legs of the knotting element with the knotting element in the open position;

positioning the second segment of the length of filamentous material in engagement with the engaging member; and moving the knotting element from the open position toward the closed position to fixedly secure the second segment of the filamentous material to the knotting element to effect a knot in the filamentous material.

* * * * *